(12) United States Patent
Romero et al.

(10) Patent No.: US 8,158,683 B2
(45) Date of Patent: Apr. 17, 2012

(54) DIETARY SUPPLEMENTS CONTAINING EXTRACTS OF ARONIA AND METHODS OF USING SAME TO PROMOTE WEIGHT LOSS

(75) Inventors: Timothy J. Romero, Columbia, TN (US); Bolin Qin, Gaithersburg, MD (US); Peter J. Miller, Broomfield, CO (US)

(73) Assignee: FHG Corporation, Spring Hill, TN (US)

(*) Notice: Subject to any disclaimer, the term of this patent is extended or adjusted under 35 U.S.C. 154(b) by 62 days.

(21) Appl. No.: 12/469,456

(22) Filed: May 20, 2009

(65) Prior Publication Data

US 2010/0222422 A1  Sep. 2, 2010

Related U.S. Application Data

(62) Division of application No. 12/396,293, filed on Mar. 2, 2009, now abandoned.

(51) Int. Cl.
*A61K 36/82* (2006.01)
*A61K 36/752* (2006.01)
*A61K 36/50* (2006.01)
*A61K 36/00* (2006.01)

(52) U.S. Cl. ......... 514/729; 424/725; 424/736; 424/739

(58) Field of Classification Search .................. None
See application file for complete search history.

(56) References Cited

U.S. PATENT DOCUMENTS

| | | | |
|---|---|---|---|
| 6,475,530 B1 | 11/2002 | Kuhrts | |
| 7,074,440 B2 | 7/2006 | Xiu | |
| 2003/0017997 A1* | 1/2003 | Yokota et al. ................... | 514/25 |
| 2003/0100082 A1 | 5/2003 | Lila et al. | |
| 2005/0238654 A1 | 10/2005 | Takeda | |
| 2006/0083795 A1 | 4/2006 | Shatkina et al. | |
| 2007/0003685 A1 | 1/2007 | Watanabe | |
| 2007/0116840 A1* | 5/2007 | Prakash et al. ................. | 426/548 |
| 2007/0178216 A1* | 8/2007 | Kandaswami et al. ........ | 426/597 |
| 2007/0218170 A1* | 9/2007 | Kendrick ......................... | 426/74 |
| 2007/0259057 A1* | 11/2007 | Sugita et al. .................... | 424/756 |
| 2008/0063689 A1 | 3/2008 | Farber | |
| 2008/0107787 A1* | 5/2008 | Prakash et al. ................. | 426/548 |
| 2008/0166435 A1 | 7/2008 | Pylypchuk | |
| 2008/0255226 A1 | 10/2008 | Eidenberger | |
| 2008/0299250 A1 | 12/2008 | Porsgaard | |

FOREIGN PATENT DOCUMENTS

| | | |
|---|---|---|
| EP | 1208755 B1 | 5/2002 |
| JP | 2001172191 A | 6/2001 |
| RO | 95203 | 8/1988 |

OTHER PUBLICATIONS

Zielinska-Przyjemska et al., Effects of Aronia melanocarpa Polyphenols on Oxidative Metabolism and Apoptosis of Neutrophils from Obese and Non-Obese Individuals, Acta Sci. Pol., Technol. Aliment. 2007. vol. 6, No. 3, pp. 75-87.

Jurgonski et al., Ingestion of Black Chokeberry Fruit Extract Leads to Intestinal and Systemic Changes in a Rat Model of Prediabetes and Hyperlipidemia, Plant Foods Hum. Nutr. 2008. vol. 63, pp. 176-182.

Kulling et al., Chokeberry (*Aronia melanocarpa*)—A Review on the Character Components and Potential Health Effects, Planta Med. 2008. vol. 74, pp. 1625-1634.

Strigl et al., Qualitative and Quantitative Analysis of the Anthocyans in Black Chokeberries (*Aronia melanocarpa* Michx. Ell.) by TLC, HPLC and UV/VIS—Spectrometry, Zeitschrift Fuer Lebensmittel-Untersuchung und -Forschung. 1995. vol. 201, No. 3, pp. 266-268, BIOSIS.

* cited by examiner

*Primary Examiner* — Christopher R. Tate

(74) *Attorney, Agent, or Firm* — Gifford, Krass, Sprinkle, Anderson & Citkowski, P.C.

(57) ABSTRACT

A dietary supplement composition comprising aronia extract containing at least 20% anthocyanins by dry weight. The aronia extract is derived from the aronia melanocarpa plant. The aronia extract comprises approximately 10%-30% of the dry weight of the composition. A vitamin, weight loss agent, or antioxidant is provided in the composition. The dietary supplement composition is administered orally to promote weight loss.

10 Claims, 6 Drawing Sheets

The physical and biochemical characteristics of the CONTROL, CB100 and CB200 groups at the end of the experiment

| | CONTROL | CB100 | CB200 |
|---|---|---|---|
| Body weight (g) | 525±7 | 509±5* | 502±5* |
| Body weight gain(g) | 80±3 | 61±2 * | 59±1 * |
| Epididymal adipose tissue (g) | 11.0±0.57 | 7.5±0.3* | 6.8±0.3* |
| Food intake (g/rat per day) | 28±1 | 27±2 | 27±1 |
| Serum insulin (ng/mL)) | 0.95 ±0.1 | 0.88 ±0.08 | 0.83 ±0.05 |
| Serum glucose (mmol/L) | 4.7 ±0.2 | 4.1±0.2* | 4.1±0.1* |
| Serum cholesterol (mmol/L) | 2.04 ±0.15 | 1.71±0.12* | 1.70±0.10* |
| Serum triglyceride (mmol/L) | 1.86 ±0.12 | 1.07 ±0.08* | 1.00±0.05* |
| Serum FFA (mmol/L) | 0.58 ±0.02 | 0.55±0.01 | 0.50±0.03 |
| Serum LDL-C (mmol/L) | 0.78 ±0.01 | 0.65±0.02 | 0.61±0.03* |
| Serum HDL-C (mmol/L ) | 0.50 ±0.03 | 0.55 ±0.04 | 0.57 ±0.02 |

Data are shown as mean ± SE ($n=6$), *$P<0.05$ vs. CONTROL.

FIG. 2

DIETARY SUPPLEMENTS CONTAINING EXTRACTS OF ARONIA AND METHODS OF USING SAME TO PROMOTE WEIGHT LOSS

CROSS-REFERENCE TO RELATED APPLICATION

This Application is a Divisional of U.S. Utility patent application Ser. No. 12/396,293, filed Mar. 2, 2009, entitled DIETARY SUPPLEMENTS CONTAINING EXTRACTS OF ARONIA AND METHODS OF USING SAME TO PROMOTE WEIGHT LOSS, the entirety of which is incorporated herein by reference.

STATEMENT REGARDING FEDERALLY SPONSORED RESEARCH OR DEVELOPMENT n/a

FIELD OF THE INVENTION

The present invention relates to dietary supplement compositions containing aronia extracts and method for promoting weight loss.

BACKGROUND OF THE INVENTION

Obesity and Type II diabetes are quickly becoming an epidemic in the United States. The increased incidence of these conditions has been attributed to diets characterized by high fat intake and repeated ingestion of refined foods and sugars, coupled with low fiber and vegetable intake. While obesity may be linked to lifestyle habits, obesity also impacts, and is impacted by, human physiology and neurology. A myriad of genetic, neurological, and other unknown factors are also likely to play a role in the development of obesity. While two thirds of the world's population is defined as overweight, obesity related illnesses are rapidly becoming the leaders in the world's most lethal diseases. For example, about 97 million adults in the United States are overweight, of which over 40 million are classified as obese. General obesity, known as adiposity, greatly increases the risk of many diseases such as hypertension, type 2 diabetes, coronary heart disease, stroke, gallbladder disease, osteoarthritis, sleep apnea and other respiratory problems, and endometrial, breast, prostate, and colon cancers. Also, people with higher than normal body weights suffer from a higher than normal early death rate. According to the National Institutes of Health, each year about 280,000 adult deaths in the United States may be attributed, in part, to obesity. Many treatments for the management of weight and obesity and the maintenance of weight loss exist. In fact, approximately, 40 percent of women and 24 percent of men are trying to actively lose weight at any given time. These treatments are numerous and include all sorts of diets, increased physical exercise, behavioral therapies, dietary supplementation, pharmacotherapy, hypnotherapy, surgery, or combinations of the above.

One such treatment involves the use of chemical compounds that inhibit absorption of nutrients, such as fats or carbohydrates, as an approach to reducing caloric intake. Other compounds simply work to stimulate metabolic rate through enhanced thermogenesis. However, the safety and efficacy of long-term administration of many weight loss compounds are simply unknown. Moreover, history has shown that certain biological pathways, for example, stimulating thermogenesis with compounds like ephedra or Phen-Fen®, may not be the best approach.

An additional avenue to target obesity entails the use of supplements and pharmaceuticals that target weight loss. These supplements and pharmaceuticals target appetite or satiety by using chemical messengers such as neuropeptides, CCK, Obestatin, Ghrelin, Enterostatin, Bombesin, CRF or many others. More recently the proliferator-activated receptor-gamma (PPARγ) system has evolved as a novel approach to weight loss and adipocyte differentiation. Other weight loss systems focus on regulating adipose hormones such as leptin, thyroid production, fatty acid synthase, or uncoupling certain proteins. The biological pathways involved in these regulation systems are complex and often redundant. Moreover, the body counteracts impacts on these regulation systems as it strives for homeostasis. Therefore, what is needed is a dietary supplement that is safe and effective at targeting weight loss.

One potential effective dietary supplement may be derived from the aronia fruit, which is one of the world's more obscure fruits. Aronia contains a dense concentration of anthocyanins, which are aqueous pigments that may appear as a variety of colors including, red, purple, or blue. They belong to a parent class of molecules called flavonoids, which are known for their powerful antioxidant potential. Anthocyanins occur in all tissues of higher plants, including leaves, stems, roots, flowers, and fruits. The aronia plant, which grows in areas of high UV concentrations, has developed defense mechanisms, such as phenolic anthocyanins, to help protect the plant from high UV radiation. As such, the aronia plant boasts one of the highest concentrations of antioxidant capacity. Moreover, research has shown aronia extracts to be potentially effective at reducing cardiovascular disease as well as improving muscle recovery. Aronia has also been shown to normalize the carbohydrate metabolism in diabetic rats as well as suppress the growth of certain cancer cells in rats. However, aronia's effects on adipose tissue are largely unknown. Additionally, the concentrations of anthocyanins from aronia that will promote weight less have previously been unknown. It is therefore desirable to provide a dietary supplement composition containing an aronia extract to promote weight loss and fat management as well as other health benefits.

SUMMARY OF THE INVENTION

It is to be understood that both the following summary and the detailed description are exemplary and explanatory and are intended to provide further explanation of the invention as claimed. Neither the summary nor the description that follows is intended to define or limit the scope of the invention to the particular features mentioned in the summary or in the description In accordance with an aspect, the present invention provides a dietary supplement composition including extracts of aronia containing at least 20% anthocyanins by dry weight.

In accordance with another aspect, the present invention provides a dietary supplement composition including an aronia melanocarpa extract containing at least 20% anthocyanins by dry weight. The aronia melanocarpa extract is approximately 10%-30% by dry weight of the composition. At least one vitamin, weight loss agent, or antioxidant is also included in the dietary supplement composition.

In accordance with yet another aspect, the present invention provides a method for promoting weight loss. The method includes administering composition comprising aronia melanocarpa extracts containing at least 0.01% anthocyanins by dry weight, wherein the aronia melanocarpa extract is approximately 0.01%-99.9% by dry weight of the composition.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is a table illustrating biological effects of the dietary supplement composition of the present invention;

DETAILED DESCRIPTION OF THE INVENTION

Figure 1:
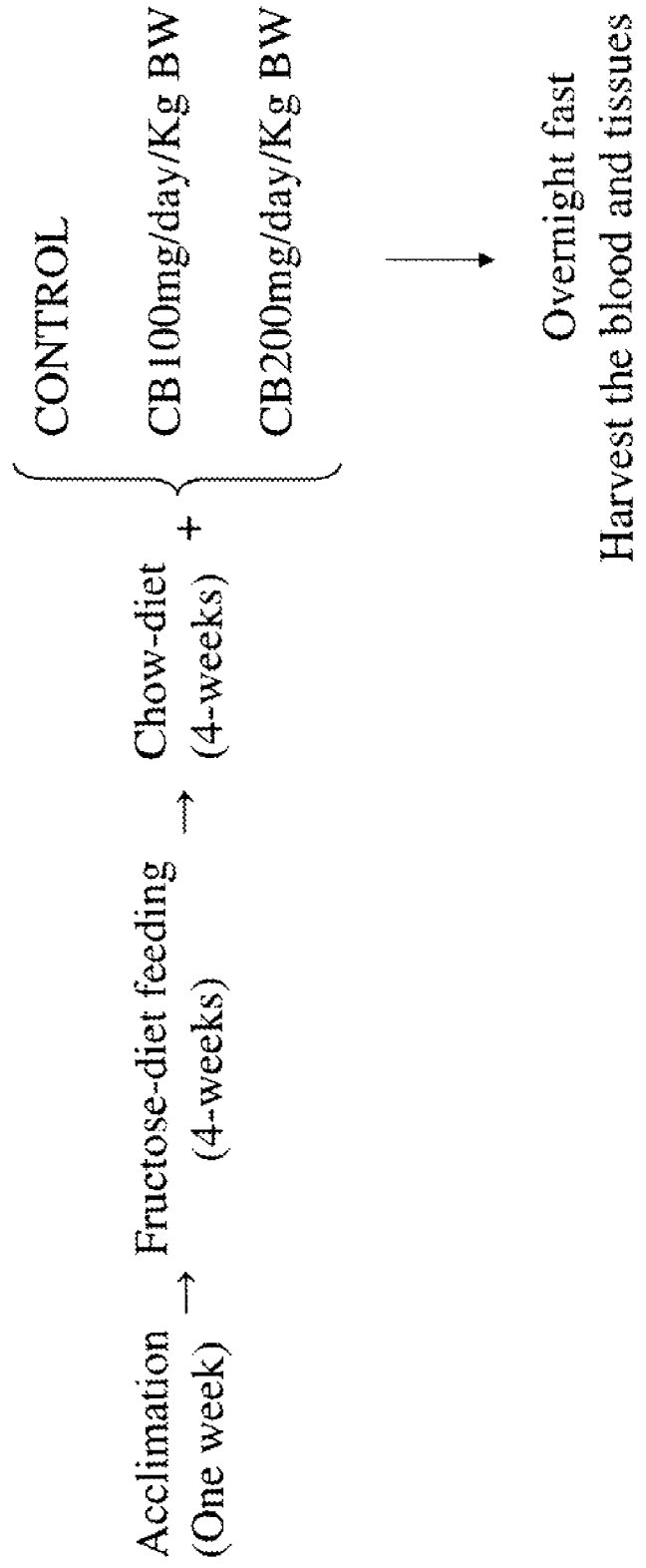
FIG. 1 is a flow chart of an exemplary method for promoting weight loss in rats in accordance with the principals of the present invention.

The present invention advantageously provides for an aronia extract composition that promotes weight loss. The Aronia plant and berries may be obtained from various parts of the world, including northern Europe and America. In an exemplary embodiment, an extract of aronia is derived from the fruit of *aronia melanocarpa*, which may contain between 0.01%-100% anthocyanins by dry weight. The aronia extract dietary supplement may be in pharmaceutical dietary supplement compositions in solid, semi-solid, or liquid dosage forms, such as, for example, tablets, chewables, suppositories, pills, capsules, powders, liquids, or suspensions, and may be provided in unit dosages suitable for a single administration. Time release preparations are also contemplated as effective dosage formulations. The compositions may include an effective amount of a selected substrate in combination with a pharmaceutically acceptable carrier and, in addition, may include other medicinal agents, pharmaceutical agents, carriers, or diluents.

In a solid composition embodiment, conventional nontoxic solid carriers may include, for example, pharmaceutical grades of mannitol, lactose, starch, magnesium stearate, sodium saccharine, talc, cellulose, glucose, sucrose and magnesium carbonate. Liquid pharmaceutically administrable compositions may, for example, be prepared by dissolving or dispersing an active compound with optimal pharmaceutical adjuvants in an excipient, such as water, saline, aqueous dextrose, glycerol, or ethanol, to form a solution or suspension. For example, the pharmaceutical composition may contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art.

In an oral administration embodiment, fine powders or granules may contain diluting, dispersing, or surface active agents. The fine powders or granules may be presented in water or in syrup, in capsules or sachets in the dry state, or in a nonaqueous solution or suspension. Suspending agents may also be included in tablets, which may include binders and lubricants in a suspension. Flavoring, preserving, suspending, thickening, or emulsifying agents may be also included to modify the taste and texture of the composition. The tablets and granules provided for oral administration may further be coated for ease of digestion.

In yet another embodiment, the aronia extract dietary supplement composition may be combined with one or more other components. Such components may include vitamins (such as vitamin A, vitamin B, vitamin C, vitamin D, or vitamin E), weight loss agents (such as synephrine, citrus aurantium, coleus, hoodia, hordenine, phenylethylamine, cinnamon extracts, evodiamine, sclareoliden, licorice oil, flavanoids, hydroxycitric acid, green tea, raspberry, guarana, yerba mate, ketone, white tea, oolong tea, fucoxanthin, or 7-keto dhea), antioxidants (such as acai, wolfberry, alpha lipoic acid, astazanthin, or fucoxanthin), or any combination of the above. In an exemplary embodiment, the dietary supplement may further include anthocyanins expressed in the form of cyanadin-3-galactose, or salts, isomers, or derivatives of cyanadin-3-galactose, which may further provide for increased weight loss.

It is further contemplated that variable dosing regiments are operative in the method of treatment. While in some instances, a single dose treatment may be effective in producing therapeutic effects, in other instances a treatment period in the range of, for example, six weeks to three months may be utilized. The composition may be administered orally, parentally, or intravenously by intramuscular, intraperitoneal, or transdermally injection. Injectables may be prepared in conventional forms, either liquid solutions or suspensions, solid forms suitable for solution or prior to injection, or as suspension in liquid prior to injection or as emulsions. The dose of the dietary supplement composition may vary depending on the age, weight, general condition of the user. For example, dosage is in the range of 1-1,000 mg of equivalent of dry aronia powder extract per day may be an effective range. The aronia extract may also comprise 0.01%-100% of the dry weight of the composition. For example, an aronia dietary supplement composition may comprise 10%-30% of the dry weight of the composition.

The examples presented below are intended to illustrate a particular embodiment of the invention and are not intended to limit the scope of the specification, including the claims, in any way.

Example #1

| | |
|---|---|
| *Aronia melanocarpa* 10% anthocyanins | 200 mg |
| Green Tea 45% egcg | 300 mg |
| Caffeine anhydrous | 100 mg |
| Evodiamine | 100 mg |
| 7-Keto DHEA | 100 mg |

Example #2

| | |
|---|---|
| *Aronia melanocarpa* 25% anthocyanins | 100 mg |
| Green Tea 45% egcg | 300 mg |
| Cinnulin PF | 250 mg |
| White Tea | 100 mg |
| *Hoodia Gordonii* | 100 mg |

Example #3

| | |
|---|---|
| *Aronia melanocarpa* 25% anthocyanins | 300 mg |
| Green Tea 45% egcg | 300 mg |
| Cinnulin PF | 250 mg |
| White Tea | 100 mg |
| *Hoodia Gordonii* | 100 mg |
| Acai Berry | 100 mg |

Example #4

| | |
|---|---|
| *Aronia melanocarpa* 25% anthocyanins | 250 mg |
| Green Tea 45% egcg | 300 mg |
| synephrine | 20 mg |
| PEA | 50 mg |
| Hordenine | 100 mg |
| caffeine | 200 mg |
| yerba mate | 200 mg |

Example #5

| | |
|---|---|
| *Aronia melanocarpa* 15% anthocyanins | 250 mg |
| Hydroxycitric acid | 500 mg |
| green coffee extract | 150 mg |
| fucoxanthin | 200 mg |
| white tea extract | 200 mg |
| guarana | 500 mg |

The efficacy and impacts of the aronia extracts on rats are illustrated below. The following abbreviations are used in the following paragraphs: CD36: Cluster of Differentiation 36; GYS: glycogen synthase; IL: interleukin; IR: insulin receptor; IRS-1: insulin receptor substrate-1; NPC1L1: Niemann-Pick C1 Like 1; PI3K: Phosphoinositide 3-kinase; PPAR: peroxisome proliferator-activated receptor; PTEN: phosphatase and tensin homolog deleted on chromosome ten; SCARB1: Scavenger receptor class B type I; SREBF1: sterol regulatory element binding transcription factor 1; SREBP: sterol regulatory element binding protein; and TNF, tumor necrosis factor.

Initially, dry extracts of from the aronia plant are concentration and standardized to contain 25% anthocyanins by dry weight, known as cellberry ("CB"), and tested on rats. As shown in FIG. 1, male rats were fed with a fructose diet four weeks. The rats were divided randomly into three groups, each group having a similar mean body weights, with six rats in each group. Control rats were fed a standard diet four weeks, and other two groups of rats were given either 100 mg or 200 mg/kg of bodyweight per day of an aronia extract containing 25% anthocyanins in the rats' drinking water. The body weight and food intake were evaluated for three-days each week, and the diet intake of each CB administered group during the experimental period was similar to that of the control group.

Now Referring to FIG. 2, after consuming the CB composition for four weeks, the body weights of two experimental groups were significantly reduced compared to the control group. Also, there was minimal statistical difference in bodyweight amongst the experimental groups treated with the CB composition. Both doses of the CB composition administered to the rats inhibited epididymal adipose tissue weight, compared with the control group. Additionally, the experimental groups treated with the CB compositions showed an improved blood glucose levels, as well decreased triglyceride, cholesterol, free fatty acids, and LDL-C concentrations. The experimental rat groups treated with CB also showed improved serum insulin and HDL-C levels. The data suggests that the administered CB composition improves the lipid disorders found in fructose-fed insulin resistant rats.

Figure 3:
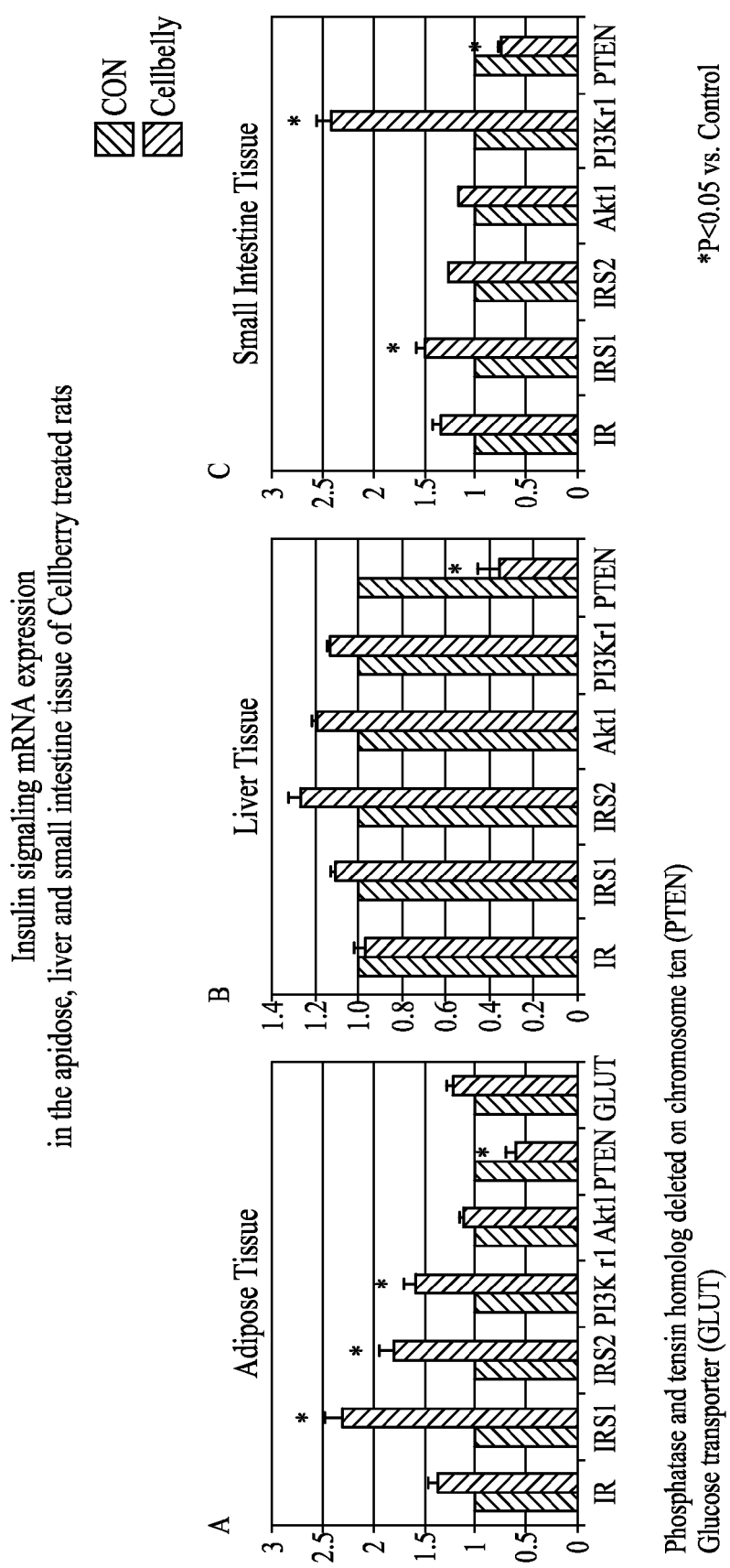
FIG. 3 is a chart illustrating effects of the dietary supplement of the present invention with respect to insulin signaling and mRNA expression in the adipose, liver, and small intestine tissue.

Now referring to FIG. 3, insulin signaling is known to affect hepatic glucose production and glucose uptake in muscle and adipose tissue, as well as influence the fat deposition in adipose tissue, hepatic and intestinal lipid metabolism. Disruption of insulin signaling can affect key cellular pathways that serve to maintain energy balance and glucose homeostasis, which can then lead to insulin resistance and progression toward various metabolic disorders, including cardiovascular disease, obesity, and type 2 diabetes. High-fructose diets often induce systemic and peripheral insulin resistance.

As shown in FIG. 3, however, consumption of the CB composition improves the mRNA expression of insulin signaling in adipose, liver and small intestine tissue. The administered CB composition increased mRNA expression of insulin receptor (35%), IRS1 (130%), IRS2 (80%), PI3Kr1 (158%), Akt1 (10%) in the adipose tissue compared with the control group. The CB treated rats also showed increased mRNA changes in the adipose tissue GLUT4, a major glucose transporter in muscle and adipose cells. The mRNA level of PTEN, a tumor suppressor, which negatively regulates insulin signaling, was also reduced significantly.

Continuing to refer to FIG. 3, consumption of the CB composition by the experimental rat group exhibit improved mRNA expression in the liver of insulin receptor (8%), IRS1 (18%), IRS2 (36%), Akt1 (19%), PI3Kr1 (13%) and decreases the expression of PTEN (65%), compared with the control group. The administered CB composition also improves the mRNA expression in the small intestine of IR (33%), IRS1 (47%), IRS2 (24%), Akt1 (15%), PI3Kr1 (140%) and decreased the expression of PTEN (27%) compared with the control group. The data suggest that CB consumption improves the mRNA expression of insulin signaling in adipose, liver, and small intestine tissue leading to improved glucose and lipid metabolism.

Figure 4:
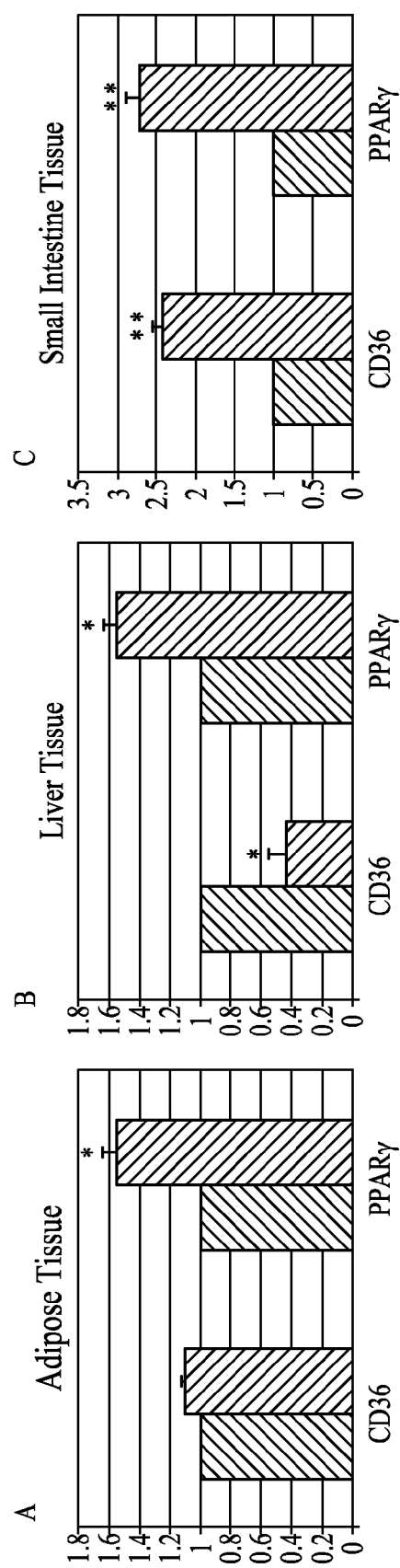
FIG. 4 is a chart illustrating effects of the dietary supplement of the present invention with respect to CD36, fatty acid transporter and PPARγ, lipid sensor, and mRNA expression in adipose, liver, and small intestine tissue.

Now referring to FIG. 4, CD36, a fatty acid translocase, is a cell-surface glycoprotein that functions as a multi-ligand receptor or transporter involved in various diverse physiological processes and disorders, including atherosclerosis, dyslipidemia, insulin resistance and diabetes. Defective function or expression of CD36 may result in dyslipidemia or insulin resistance. Moreover, an increased expression of hepatic CD36 protein in response to diet-induced obesity may exacerbate hepatic triglyceride storage and secretion. As shown in FIG. 4, the CB treated rats exhibit decreased expression of CD36 (57%) in the liver tissue, which may improve overall lipid metabolism.

Continuing to refer to FIG. 4, CD36 may also be important for chylomicron production and acute fatty acid uptake in the small intestine. In the small intestine tissue of CB administered rats, an increase in the mRNA expression of CD36 (140%) was observed. This result suggests that the CB composition may regulate lipid absorption and transfer.

PPARγ is expressed in high levels in adipose tissue and plays a role in increasing insulin sensitivity as well as in promoting fatty acid uptake into adipocytes and adipocyte differentiation. The net effect of these processes is to increase triglyceride storage in adipocytes, reducing delivery of fatty acids to the liver. As shown in FIG. 4, the CB administered rats exhibit an increased PPARγ expression in adipose and liver tissue of the CB treated rats. The CB administered rats also exhibit and increased mRNA expression of PPARγ (170%) in the small intestine tissue. The data suggests that the CB composition enhances PPARγ expression, which improve insulin sensitivity, thereby regulating lipid metabolism in these tissues.

Figure 5:
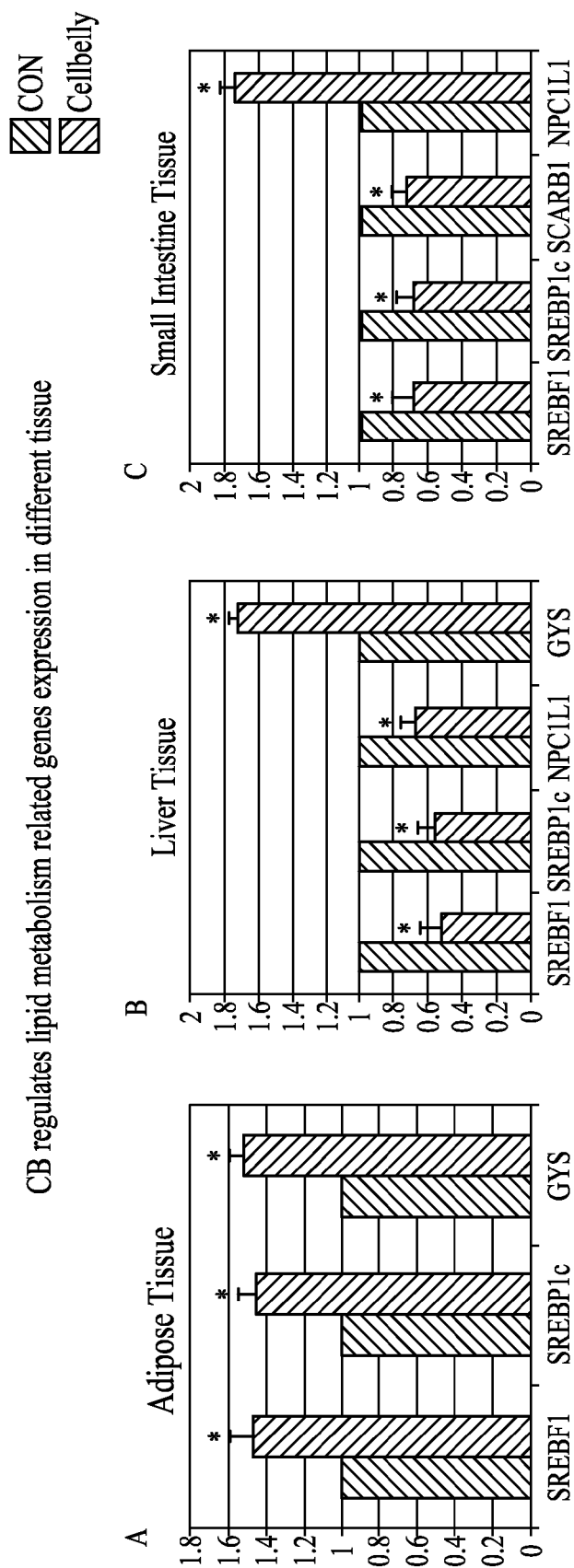
FIG. 5 is a chart illustrating effects of the dietary supplement of the present invention with respect to mRNA expression related to lipid metabolism in adipose, liver and small intestine tissue.

Now referring to FIG. 5, sterol regulatory element binding protein (SREBP)1c is a master regulator of lipogenic gene expression in adipose and liver tissue. The expressions of adipogenesis-related genes, including SREBP1c, may decrease in the adipose of animal tissue exposed to a long term high fat diet. As shown in FIG. 5, the CB administered rats exhibit enhanced mRNA expression of SREBP1c (35%) in the adipose tissue compared with the control group. The CB administered rats also exhibit enhanced mRNA expression of sterol regulatory element binding transcription factor 1 (SREBF1) (47%), which may play an important role in regulation of adipose fat deposition. Moreover, the CB administered rats exhibit increased adipose (51%) and hepatic (72%) glycogen synthase.

Continuing to refer to FIG. 5, SREBP1c also has a crucial role in the regulation of triglyceride accumulation in the liver and the overproduction of intestinal derived apoB48. An increase of SREBF1 may be associated with greater concentrations of triglycerides. The CB administered rats exhibit decreased mRNA expression of SREBP1c (44%) and SREBF1 (48%) in the liver as well as SREBF1 (32%) in the small intestine tissue.

Scavenger receptor class B type I (SCARB1) is expressed in enterocyte brush border membranes mainly at the top of intestinal villosities and in the proximal part of intestine where cholesterol absorption mainly occurs. Over expression of SCARB1 in the small intestine may increase intestinal absorption of both cholesterol and triglycerides. As shown in FIG. 5, the CB administered rats exhibit decreased mRNA expression of SCARB1 (27%) in the small intestine tissue.

Niemann-Pick C1 Like 1 (NPC1L1) is a protein localized in jejunal enterocytes that is critical for small intestinal cholesterol absorption. Inactivation of NPC1L1 may cause multiple lipid transport defects and protects against diet-induced hypercholesterolemia. The CB administered rats exhibit significantly enhanced NPC1L1 expression in the small intestine. In contrast to the intestinal tissue, the CB administered rats exhibit a decreased NPC1L1 expression in liver tissue. The data from the adipose, liver, and small intestinal tissue show that CB consumption may be useful to regulate gene expression related to adipogenesis, hepatic, and small intestinal lipid metabolism.

Figure 6:
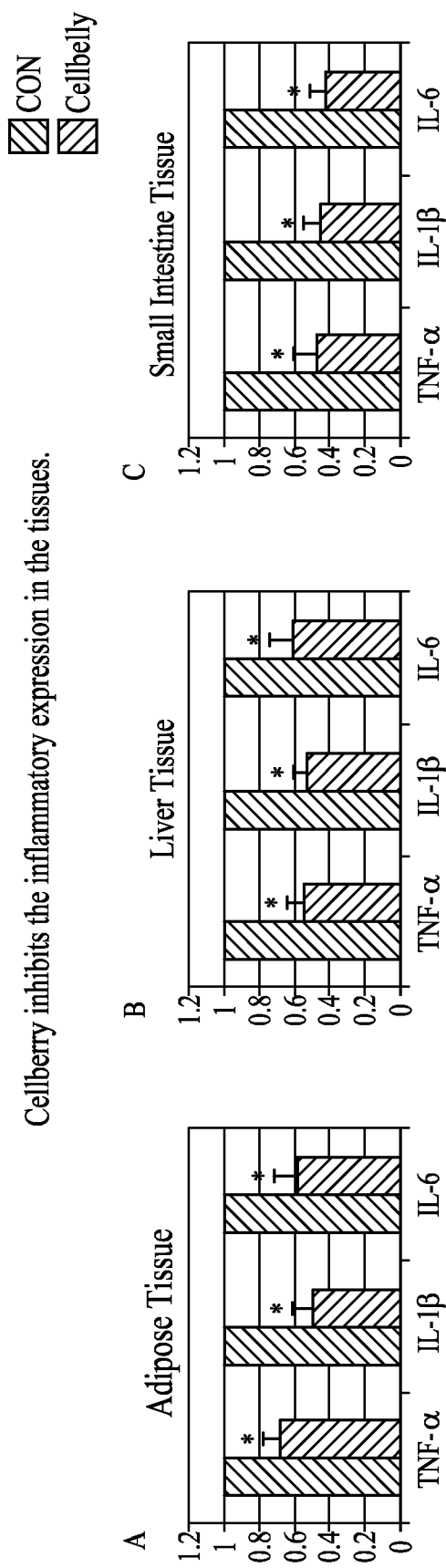
FIG. 6 is a chart illustrating effects of the dietary supplement on inflammatory factor mRNA expression in adipose, liver and small intestine tissue.

Now referring to FIG. 6, obesity and inflammation are highly integrated processes in the pathogenesis of insulin resistance, diabetes, and atherosclerosis. Obesity may induce a pro-inflammatory state, which may cause or worsen insulin resistance in adipose tissue, liver, and the small intestine. In abdominal obesity, the high mass of visceral adipose tissue may be extremely active metabolically and secrete many inflammatory cytokines and chemokines having effects at local and systemic level. Insulin resistance is associated with a state of chronic low-grade inflammation. Several mediators released from various cell types, including immune cells and adipocytes, have been identified as being involved in the development of insulin resistance. Among those are several pro-inflammatory cytokines such as tumor necrosis factor (TNF)-α, interleukin (IL)-1β, IL-6, and various adipocytokines. The inflammatory factor TNF-α may induce systemic, small intestinal, and hepatic insulin resistance, as well as stimulate apoB48 and systemic dyslipidemia.

As shown in FIG. 6, the CB administered rats exhibit decreased mRNA expression of IL-1β (51%), TNF-α (25%), and IL-6 (42%) in the adipose tissue. The CB administered rats also exhibit decreased mRNA expression of IL-1β (47%), TNF-α (46%), IL-6 (39%) in the liver, as well as decreased mRNA expression of IL-1β (53%), TNF-α (55%), IL-6 (58%) in the small intestine tissue, compared with the control group.

These results demonstrate that CB consumption may improve blood glucose, serum lipid profiles, adipose tissue mass and bodyweight gain by regulating the multiple genes in adipogenesis, glucose, lipid and inflammatory pathways. CB consumption may also be beneficial in humans for managing metabolic syndrome including obesity, dyslipidemia and insulin resistance.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of promoting weight loss in a human in need thereof comprising:
    Administering to the human a dosage of a composition comprising an aronia melanocarpa extract, the aronia melanocarpa extract containing at least 10% anthocyanins by dry weight; the composition further including green tea.

2. The method of claim 1, wherein the green tea is provided at 300 mg per dosage unit.

3. The method of claim 2, where the green tea contains 45% epigallocatechin gallate (egcg) by dry weight.

4. The method of claim 1, wherein the composition is administered at least once a day.

5. The method of claim 1, wherein the composition is administered in powdered form.

6. The method of claim 1, wherein the composition is administered in liquid form as a suspension.

7. The method of claim 1, wherein the composition further includes cinnamon.

8. The method of claim 1, wherein the composition further includes raspberry ketone.

9. The method of claim 1, wherein the composition further includes citrus aurantium.

10. The method of claim 1, wherein the composition further includes white tea.

* * * * *

UNITED STATES PATENT AND TRADEMARK OFFICE
CERTIFICATE OF CORRECTION

| | | |
|---|---|---|
| PATENT NO. | : 8,158,683 B2 | Page 1 of 1 |
| APPLICATION NO. | : 12/469456 | |
| DATED | : April 17, 2012 | |
| INVENTOR(S) | : Tim Romero et al. | |

It is certified that error appears in the above-identified patent and that said Letters Patent is hereby corrected as shown below:

Column 2, Line 39, Delete "less" Insert --loss--

Column 2, Line 53, After Description Insert --.--

Column 5, Line 60, Delete "of"

Column 5, Line 63, After diet Insert --for--

Column 5, Line 66, After diet Insert --for--

Column 6, Line 17, After well Insert --as--

Column 7, Line 18, Delete "and" Insert --an--

Signed and Sealed this
Twenty-eighth Day of August, 2012

David J. Kappos
*Director of the United States Patent and Trademark Office*